US008377881B2

(12) United States Patent
Moonen et al.

(10) Patent No.: US 8,377,881 B2
(45) Date of Patent: Feb. 19, 2013

(54) COMPOSITIONS AND METHODS FOR REDUCING SCAR FORMATION IN WOUND HEALING

(75) Inventors: Peter Jozef Jacobus Moonen, Susteren (NL); Christiaan Peter Maria Reutelingsperger, Maastricht (NL); Ad Vermaire, Kattendijke (NL)

(73) Assignee: MosaMedix B. V., Kattendijke (NL)

( * ) Notice: Subject to any disclaimer, the term of this patent is extended or adjusted under 35 U.S.C. 154(b) by 133 days.

(21) Appl. No.: 12/935,900

(22) PCT Filed: Apr. 1, 2009

(86) PCT No.: PCT/NL2009/050169
§ 371 (c)(1),
(2), (4) Date: Dec. 14, 2010

(87) PCT Pub. No.: WO2009/123454
PCT Pub. Date: Oct. 8, 2009

(65) Prior Publication Data
US 2011/0091527 A1    Apr. 21, 2011

Related U.S. Application Data

(60) Provisional application No. 61/041,278, filed on Apr. 1, 2008.

(51) Int. Cl.
*A61K 38/00* (2006.01)
(52) U.S. Cl. ...................................................... 514/12.1
(58) Field of Classification Search ............... 514/12, 514/12.1
See application file for complete search history.

(56) References Cited

U.S. PATENT DOCUMENTS 5,360,789 A    11/1994   Nakao et al.

FOREIGN PATENT DOCUMENTS

| WO | WO-00/44443 A2 | 8/2000 |
| WO | WO 2006/003488 A2 | 1/2006 |
| WO | WO 2007/069895 A1 | 6/2007 |

OTHER PUBLICATIONS

Kenis et al., Cell. Mol. Life Sci., 64, 2859-2862, 2007.*
Hiroshi Nakao et al.. "A new function of calphobindin I (annexin V) Promotion of both migration and urokinase-type plasminogen activator activity of normal human keratinocytes"; Eur. 1. Biochem. (1994) vol. 223, pp. 901-908.
Masanao Watanabe et al.; "Promotion of Corneal Epithelial Wound Healing In Vitro and In Vivo by Annexin A5", Invest. Ophthalmol Vis Sci. 2006;47, No. 5:1862-1868.
Watanabe M etal: "Human Annexin A5 Promotes the Migration of Rabbit Corneal Epithelial Cells" Invest Ophthalmol Vis Sci 2003; 44: E-abstract 3823.
Kondo S etal: "Effect of Human Annexin A5 Eye Drops on Corneal Epithelial Wound Healing in Rabbits", Invest Ophthalmol Vis Sci 2003; 44: E-abstract 3831.
International Search Report for International Application No. PCT/NL2009/050169 with a completion date of Aug. 31, 2009.

* cited by examiner

*Primary Examiner* — Maryam Monshipouri
(74) *Attorney, Agent, or Firm* — Gilberto M. Villacorta; Sunit Talapatra; Foley & Lardner LLP

(57) ABSTRACT

The invention pertains to a method of reducing scar formation during wound healing by administering a phosphatidylserine-binding compound, in particular an annexin, to a subject in need thereof. The healing wound may be a skin damage, but it may also be a myocardium e.g. which is at risk of suffering or is recovering from a heart failure.

22 Claims, No Drawings

COMPOSITIONS AND METHODS FOR REDUCING SCAR FORMATION IN WOUND HEALING

This application is a U.S. national stage application of International Application No. PCT/NL2009/050169, filed Apr. 1, 2009, which claims priority from U.S. Provisional Application No. 61/041,278, each of the above-identified applications is incorporated herein by reference in its entirety.

FIELD OF THE INVENTION

The present invention relates to compositions and interventions, which aim to improve wound healing by reducing fibroblast formation and extra-cellular matrix deposition and hence scarring.

BACKGROUND OF THE INVENTION

Scar formation during wound healing is a cosmetically undesired process, especially if the scars are formed on the face and other conspicuous or identity-determining parts of the body. Scar formation can also have health implications. As a prominent example, myocardial scar formation occurring after myocardial infarction impairs cardiac function by inducing cardiac remodeling, reducing cardiac compliance and compromising normal electrical conduction across the heart.

When we are injured, the body launches a complex rescue operation. Specialized cells called fibroblasts present just beneath the surface of the skin come into action, enter the provisional wound matrix (the clot) and start secreting collagen to close the wound as fast as possible. This matrix is initially soft and loaded with growth factors. The fibroblasts "crawl" around the matrix, pulling and reorganizing the fibers. The matrix grows stiffer, and at a certain point, the fibroblasts stop migrating and change into powerful contractile cells, anchoring themselves to the matrix and pulling the edges of the wound together.

Although this process will heal a wound quickly, it can also lead to a build-up of fibrous tissue. Following trauma to vital organs such as the heart, lung, liver and kidney, overzealous fibroblasts can continue to build fibrous strands, leading to scar tissue formation that can impair the organ's function. This condition, called "fibrosis", can be fatal. Fibroblasts are also the culprits in problems caused by implants; if the implant is too smooth, it never becomes properly incorporated into the connective tissue. However, if it is too rough, scar tissue develops around it and the tissue will not function properly. Occasionally, following plastic surgery, unsightly excessive scar tissue can develop in the skin as well. The process can also cause problems in mesenchymal stem cell cultures; if the culture's substrate is stiff, considerable efforts have to be made to prevent the stem cells from turning prematurely into fibroblasts instead of the desired cell type. Controlling the rigidity of the cell culture is therefore critical.

A fibroblast is a type of cell that synthesizes and maintains the extracellular matrix of many animal tissues. Fibroblasts provide a structural framework (stroma) for many tissues, and play a critical role in wound healing. They are the most common cells of connective tissue in animals.

The main function of fibroblasts is to maintain the structural integrity of connective tissues by continuously secreting precursors of the extracellular matrix. Fibroblasts secrete the precursors of all the components of the extracellular matrix, primarily the ground substance and a variety of fibers. The composition of the extracellular matrix determines the physical properties of connective tissues.

Fibroblasts are morphologically heterogeneous with diverse appearances depending on their location and activity. Though morphologically inconspicuous, ectopically transplanted fibroblasts can often retain positional memory of the location and tissue context where they had previously resided, at least over a few generations.

Unlike the epithelial cells lining the body structures, fibroblasts do not form flat monolayers and are not restricted by a polarizing attachment to a basal lamina on one side, although they may contribute to basal lamina components in some situations (e.g. subepithelial myofibroblasts in intestine may secrete the α-2 chain carrying component of the laminin, which is absent only in regions of follicle associated epithelia which lack the myofibroblast lining). Fibroblasts can also migrate slowly over substratum as individual cells, again in contrast to epithelial cells. While epithelial cells form the lining of body structures, it is fibroblasts and related connective tissues which sculpt the "bulk" of an organism.

Nakao and colleagues studied the effects of annexin A5 on normal human keratinocytes (NHK) in vitro and in a surgical wound assays for reepithelialization (Nakao et al.: A new function of calphobindin I (annexin A5): Promotion of both migration and urokinase-type plasminogen activator activity of normal human keratinocytes; Eur. J. Biochem. (1994) 223: 901-908). These in vitro studies showed promotion by Calphobindin of both uPA synthesis of epithelial keratinocytes and their migration (but not proliferation). Topical application of Calphobindin to cutaneous wounds in rat skin appeared to promote reepithelialization in these experiments.

Watanabe and colleagues have reported that Annexin A5 promotes corneal epithelial wound healing both in vitro and in vivo and that upregulation of uPA release from corneal epithelial cells may contribute to this effect of annexin A5 (Watanabe et al.; Promotion of Corneal Epithelial Wound Healing In Vitro and In Vivo by Annexin A5; Invest. Ophthalmol. Ms. Sci. 2006 47: 1862-1868).

However, these authors do not suggest to use annexins pharmaceutically in the context of scar formation.

SUMMARY OF THE INVENTION

It was found according to the invention, that scar formation occurring during wound healing of a mammalian subject can be prevented or reduced by administering a phosphatidylserine-binding compound to the mammalian subject.

The reduction of scar formation can be carried out as part of cosmetic treatment. Alternatively, it can be carried out as part of plastic surgery, or as part of a post-treatment of plastic surgery.

The reduction of scar formation can also be carried out as part of a treatment for prevention of heart failure.

DETAILED DESCRIPTION OF THE PREFERRED EMBODIMENTS

In a first aspect, the invention concerns the use of a phosphatidylserine-binding compound for preventing, inhibiting or otherwise reducing scar formation in the skin of a mammalian subject. Pharmaceutically suitable formulations are especially formulations for topical or intravenous administration, such as ointments, creams, plasters and injectable solutions or suspensions.

The reduced scar formation is relevant in conditions where excessive fibrosis may occur. Such condition may be a form of pathological scarring of the skin (e.g. hypertrophic scarring or keloids) or an internal scar or fibrosis. Alternatively the condition may be a fibrotic disease or disorder also as mentioned above. Other conditions that may be treated include fibrotic disorders of the skin such as: Sclerodemia, Systemic sclerosis, Crest Syndrome, Tuberous sclerosis with skin patches, Familial cutaneous collagenoma, metabolic and immunologic disorders of the skin (porphyria cutanea tarda, chronic graft versus host disease), Eosinophilic facsitis, Discoid lupus erythematosus, Dermatomyositis, Mixed connective tissue disease, Drug-induced skin fibrosis, Peyronie's disease, Oral submucous fibrosis, Fibrosis-induced following dietary and environmental exposures, fibrotic disorders of other organs including: Pulmonary/cardiac fibrosis, Liver fibrosis/cirrhosis, Renal fibrosis, GI tract fibrosis, Drug induced fibrosis (e.g. post organ transplantation), Central and peripheral nervous system fibrosis, Vascular system (veins and arteries) fibrosis, Male and female genito-urinary tract fibrosis, and Gynaecological fibrosis (fallopian tube fibrosis, uterine fibromas).

In a preferred embodiment, the invention is concerned with preventing myocardial scar formation, thus reducing the chance of heart failure. Thus, the invention concerns a phosphatidylserine-binding compound as defined above for preventing, inhibiting or otherwise reducing fibrosis in the heart of a mammalian subject. Pharmaceutically suitable formulations are especially formulations for intravenous and intrapericardial administration, such as injectable solutions or suspensions.

The reduction of fibrosis in the heart can be part of a program of treating mammalian subjects suffering from myocardial infarction or from the effects thereof. Such program comprises the administration of annexin A5 or a derivative thereof for example to a patient that has experienced myocardial infarction in a period of seven days prior to annexin A5 administration. The amount of annexin A5 or derivative thereof may range from 0.002 mg/kg to 10 mg/kg body weight, more particularly 0.02 to 2 mg/kg body weight.

Alternatively or in addition, phosphatidylserine-binding compound can be administered to a mammalian subject as part of a treatment to reduce the chance on development of heart failure.

The phosphatidylserine-binding compound is believed to inhibit or reduce the load of fibroblasts in the injured and surrounding tissue, and hence to reduce or smoothen the formation of connective tissue and reducing scar.

As described herein, a phosphatidylserine binding-compound is a compound, in particular a proteinaceous compound capable of binding to phosphatidylserine, especially with a dissociation constant for phosphatidyl serine $Kd<10^{-6}$ M, preferably a $Kd<10^{-8}$M, and preferably not binding to phosphatidylcholine, especially having a dissociation constant for phosphatidylcholine $Kd>10^{-7}$, preferably $>10^{-6}$. Examples thereof are compounds of the so-called annexin family and derivatives of annexins, including the human annexin described in WO 2007/069895, such as Annexin A4, Annexin A5 and Annexin A8. In particular, the phosphatidylserine-binding compound is an Annexin A5 or a derivative thereof.

As a result of its capability of recognizing phosphatidylserine exposed on the cell surface of cells which are present at healing wounds, the phosphatidylserine binding-compound which is administered will concentrate at the site of the healing wound.

The annexin, such as annexin A5, may be the non-modified form, having the amino acid sequence (in case of A5) of FIG. 1 of WO 2007/069895, which is incorporated herein by reference. As such, the annexin may be a native annexin, or it may be a recombinant annexin produced by methods known in the art. The non-modified annexin may or may not comprise an N-terminal methionine residue or other leader sequence.

The annexin may also be in a modified form, wherein one or more amino acids are substituted. A suitable example of a modified annexin is an annexin having a single cysteine residue at the concave side of the annexin, such as a cysteine residue at one of the N-terminal positions 1-15 of the amino acid sequence of annexin A5. Such modifications are described e.g. in WO 2006/003488, which is incorporated herein by reference. Such modification of the annexin compounds allows the compound to be covalently bound to biologically active compounds capable of assisting in the reduction of extracellular matrix formation, or capable of performing another desired biological function. As an alternative, the annexin may be coupled to a nanoparticle, which can be used as a carrier for biologically active compounds and increase the payload of annexin-coupled biological compounds. Examples of such biologically active compounds include anti-infective compounds such as antibiotics (tetracyclin, minocyclin, erythromycin, clindamycin, metronidazol, sulfacetamide, amoxicillin, trimetroprim, quinones), anti-apoptotic compounds (caspase inhibitors, calpain inhibitors, cathepsin inhibitors), anti-inflammatory compounds such as steroids, anti-matrix metalloproteinases (TIMP-1, 2, 3 and 4), especially small (MW 150-750) anti-MMP molecules such as derivatives of methylpentanamide (marimastat), prinomastat (AG-3340), peptide-based inhibitors (batimastat, ilomastat (GM6001), FN-439), hydroxamic based inhibitors (RO113-2908), plasmin inhibitors (alpha2-plasmin inhibitor, amino acid based inhibitors from snake venom, peptide based inhibitors), anti-viral compounds. The nanoparticles can be e.g. of solid, semi-solid or liquid lipids nature, e.g. following conventional lipid nanoparticle technology, and emulsions of polymers. Examples of suitable nanoparticles include liposomes. The covalent binding can be performed using known methods, such as those described in WO 2006/003488 and WO 2007/069895, for example by coupling of the cysteine residue through a maleimide-activated linker to the biologically active compound or the nanoparticle carrying such active compound.

The phosphatidylserine binding-compound is administered to a mammalian, especially human, subject in an effective amount in a pharmaceutically suitable formulation. An effective amount is determined in accordance with the condition and general status, age, body weight, administration form, etc. of the patient. It can be e.g. between 0.15 mg-150 mg per patient per day, or in particular between 0.5 and 50 mg per patient per day or more in particular between 1 and 20 mg per patient per day. In case of topical administration, the dosage amount can in particular be e.g. between 0.15 and 50, more in particular between 0.25 and 20, most especially between 0.5 and 10 mg per patient per day. In case of systemic (e.g. intravenous) administration, the dosage amount can in particular be e.g. between 0.5 and 200 mg, more in particular between 1 and 100 mg, most especially between 5 and 50 mg per patient per day. It is preferred to express the dosage amount in mg per kg body weight per day. Thus, the dosage amount is e.g. 0.002 mg/kg-10 mg/kg per day, or in particular between 0.01 and 1 mg/kg per day or more in particular between 0.02 and 0.4 mg/kg per day. For systemic administration, the preferred dosage amount is 0.01-5, more preferably 0.02-2.5, most preferably 0.05-1 mg/kg.

The pharmaceutically suitable formulation can generally be a formulation suitable for systemic (i.e. non-topical) administration. Suitable administration forms comprise inhalation, intravenous injection, intra-pericardial injection, intradermal injection, and a transdermal drug patch.

Intra-pericardial administration can be performed using endoscopic (thoracoscopic or laparoscopic) techniques using minimal incisions and local visual control of an injection through the pericardium. Alternatively, intra-pericardial administration may be performed using injection without incision and external visual control. Intra-pericardial administration is described e.g. in WO 2000/44443.

Injection forms comprise aqueous solutions, dispersions and the like, for example lipid nanoparticles suspensions, containing phosphatidylserine binding compound at a concentration ranging from 0.1 mg/ml to 50 mg/ml. The carrier medium is advantageously an iso-osmolaric (or isotonic) solution containing physiologic salt and/or sugar levels.

Systemic, including intravenous, administration can be effected using a continuous administration (drip infusion) or by repeated or single (bolus) injections.

Another form of systemic injection is through a transdermal device patch, allowing passage of the drug through the skin into the blood circulation. Transdermal administration can be combined with topical application through appropriate patches.

The pharmaceutically suitable formulation can in general also be a formulation suitable for topical administration. Suitable administration forms comprise creams, ointments, gels and lotions. Creams and lotions are emulsions of oil in water and contain emulsifiers. Phosphatidylserine binding compounds can be formulated in creams and lotion at a concentration ranging from 0.1 mg/ml to 50 mg/ml, especially 1-20 mg/ml. The emulsions may contain pH-stabilizing agents, fragrances, preservatives, antioxidants, and color additives. Gels are based on hydrophilic polymers such as polysaccharides, acrylic polymers, oxyethylene, oxypropylene and the like polymers. Phosphatidylserine-binding compounds can be formulated in gels at a concentration ranging from 0.1 mg/ml to 50 mg/ml. The gels may contain pH stabilizing agents, fragrances, preservatives, antioxidants, and color additives.

The invention also relates to a pharmaceutical composition, in which the phosphatidyl-serine-binding compound is formulated with pharmaceutically acceptable excipients. Examples of such excipients include water, cations, anions, stabilizing proteins, stabilizing carbohydrates, and chelating agents etc.

The reduction of scar formation can be carried out as part of a cosmetic treatment, especially where the scar is present at exposed areas, such as the face. Alternatively, it can be carried out as part of plastic surgery, or as part of a post-treatment of plastic surgery, where the plastic surgery results in, or has the risk of resulting in, scar formation. The administration forms and dosages can be the same for cosmetic treatment or plastic surgery as for the therapeutic treatment as described above, although topical administration will often be preferred.

EXAMPLE

This experiment was designed to study the effect of annexin A5 on infiltration of fibroblasts and the deposition of connective tissue in the skin that was injured by incision with a scalpel. This design is a general model for wound healing and represents fundamental processes of wound healing as they can occur in the heart following for example myocardial infarction.

Mice were anaesthesized using standard techniques. An incision of the dorsal skin was made with a scalpel. A mini osmotic pump was implanted dorsally and subcutaneously. The mini osmotic pumps were filled either with a solution of annexin A5 or a saline solution. The administration dose was 2.8 mg/kg per day. The incision of the skin was stitched and the mice were allowed to move around freely and drink and eat ad libitum.

Two weeks later the mice were sacrificed and samples of the skin were taken for histochemical analysis. The samples were fixed with paraformaldehyde and further processed according to standard techniques.

Paraffin embedded samples were sectioned and the sections were further processed according to standard techniques. The sections were stained with hematoxylin & eosin (H&E), and standard connective tissue staining techniques. Fibroblasts were detected in the H&E stained sections.

Histochemical analysis revealed that annexin A5 reduced both the infiltration and connective tissue deposition in the area of the incised and subsequently stitched skin compared to mice that were treated with the blanc. The analyses also showed that scar formation was remarkably reduced. Reduced scar formation likely results from decreased infiltration of fibroblasts and diminished connective tissue deposition.

In this example annexin A5 was applied through a mini osmotic pump that releases annexin A5 into the subcutaneous interstitium. Annexin A5 can also be applied topically using carrier systems such a creams, lotions and gels, locally through subcutaneous injection and systemically through intravenous injection.

References

Nakao et al. U.S. Pat. No. 5,360,789 (Nov. 1, 1994)

Hiroshi Nakao, Masanao Watanabe and Masahiro MA: A new function of calphobindin I (annexin V) Promotion of both migration and urokinase-type plasminogen activator activity of normal human keratinocytes ; Eur. J. Biochem. (1994) vol. 223, pp 901-908.

Masanao Watanabe, Shoichi Kondo, Ken Mizuno, Wataru Yano, Hiroshi Nakao, Yukio

Hattori, Kazuhiro Kimura, and Teruo Nishida; Promotion of Corneal Epithelial Wound Healing In Vitro and In Vivo by Annexin A5 Invest. Ophthalmol Vis Sci. 2006; 47:1862-1868.

The invention claimed is:

1. A method for reducing scars comprising administering to scar tissue an effective amount of a phosphatidylserine-binding compound.

2. The method according to claim 1, wherein the administering is systemic administering.

3. The method according to claim 2, wherein the administering is through intravenous injection.

4. The method according to claim 1, wherein the administering is topical via a cream, gel or lotion.

5. The method according to claim 1, wherein the phosphatidylserine-binding compound is an annexin or a derivative thereof.

6. The method according to claim 5, wherein the phosphatidylserine-binding compound is annexin A5 or a derivative thereof.

7. The method according to claim 5, wherein the annexin or derivative thereof is an annexin bearing a single cysteine residue at the concave side of the molecule.

8. The method according to claim 5, wherein the phosphatidylserine-binding compound is coupled to a nanoparticle.

9. The method according to claim 8, wherein said nanoparticle is a liposome.

10. The method according to claim 5, wherein the annexin is coupled to an anti-infective, anti-inflammatory, anti-matrix metalloproteinase agent, or an anti-apoptotic agent, either directly or through a nanoparticle.

11. The method according to claim 10, wherein the anti-infective is an antibiotic.

12. The method according to claim 10, wherein the anti-inflammatory is a steroid.

13. The method according to claim 10, wherein the anti-matrix metalloproteinase belongs to the class of small chemical compounds.

14. The method according to claim 1, wherein the phosphatidylserine-binding compound is administered in a daily dose within the range of 0.15 mg-150 mg.

15. A method for reducing scars, comprising administering to a person in need thereof of an effective amount of a phosphatidylserine-binding compound, wherein said scars result from a heart trauma.

16. A method for preventing, inhibiting or reducing heart fibrosis, comprising administering to a mammalian subject in need thereof, an effective amount of a phosphatidylserine-binding compound.

17. The method according to claim 16, wherein the phosphatidylserine-binding compound is administered through intravenous injection.

18. The method according to claim 16, wherein the phosphatidylserine-binding compound is administered through intrapericardial injection.

19. The method according to claim 16, wherein the mammalian subject suffers from myocardial infarction.

20. The method according to claim 18, wherein the compound is administered to the mammalian subject as part of a treatment to reduce the chance of development of heart failure.

21. The method according to claim 1, wherein the phosphatidylserine-binding compound is administered subsequent to a cardiovascular intervention procedure, cosmetic treatment, plastic surgery, or as part of post-treatment of plastic surgery.

22. A method for reducing scars, comprising systemically administering to a person in need thereof an effective amount of a phosphatidylserine-binding compound.

* * * * *

UNITED STATES PATENT AND TRADEMARK OFFICE
CERTIFICATE OF CORRECTION

PATENT NO. : 8,377,881 B2  Page 1 of 1
APPLICATION NO. : 12/935900
DATED : February 19, 2013
INVENTOR(S) : Moonen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 208 days.

Signed and Sealed this
First Day of September, 2015

Michelle K. Lee
*Director of the United States Patent and Trademark Office*